(12) United States Patent
Kurihara et al.

(10) Patent No.: US 10,961,529 B2
(45) Date of Patent: *Mar. 30, 2021

(54) BARCODING NUCLEIC ACIDS

(71) Applicant: Takara Bio USA, Inc., Mountain View, CA (US)

(72) Inventors: Takao Kurihara, Mountain View, CA (US); Emmanuel Kamberov, Mountain View, CA (US); Tim Tesmer, Mountain View, CA (US); John Langmore, Mountain View, CA (US)

(73) Assignee: Takara Bio USA, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/183,107

(22) Filed: Nov. 7, 2018

(65) Prior Publication Data
US 2019/0153434 A1 May 23, 2019

Related U.S. Application Data

(63) Continuation of application No. 14/438,280, filed as application No. PCT/US2013/068468 on Nov. 5, 2013, now Pat. No. 10,155,942.

(60) Provisional application No. 61/722,357, filed on Nov. 5, 2012.

(51) Int. Cl.
*C12N 15/00* (2006.01)
*C12N 15/10* (2006.01)
*C12Q 1/6855* (2018.01)

(52) U.S. Cl.
CPC ....... *C12N 15/1065* (2013.01); *C12Q 1/6855* (2013.01); *C12Q 2525/155* (2013.01); *C12Q 2525/191* (2013.01); *C12Q 2525/301* (2013.01); *C12Q 2563/179* (2013.01)

(58) Field of Classification Search
None
See application file for complete search history.

(56) References Cited

U.S. PATENT DOCUMENTS

| | | | |
|---|---|---|---|
| 5,858,656 A | 1/1999 | Deugau et al. | |
| 5,935,793 A | 8/1999 | Wong | |
| 6,261,782 B1 | 7/2001 | Lizardi et al. | |
| 7,537,897 B2 | 5/2009 | Brenner et al. | |
| 7,803,550 B2 * | 9/2010 | Makarov ................. | C12P 19/34 435/6.1 |

(Continued)

FOREIGN PATENT DOCUMENTS

| | | | |
|---|---|---|---|
| WO | WO 2010/030683 | 3/2010 | |
| WO | WO-2010030683 A1 * | 3/2010 | ......... C12N 15/1093 |

(Continued)

OTHER PUBLICATIONS

Zhang Y. (2013) Pre-miRNA. In: Dubitzky W., Wolkenhauer O., Cho KH., Yokota H. (eds) Encyclopedia of Systems Biology. Springer, New York, NY.*

(Continued)

*Primary Examiner* — Aaron A Priest
(74) *Attorney, Agent, or Firm* — Kathleen Y. Rao; Bret E. Field; Bozicevic, Field & Francis LLP

(57) ABSTRACT

Methods of barcoding nucleic acids, such as genomic DNA, are provided herein. In some embodiments, a fragment of genomic DNA may comprise a first and a second barcode.

6 Claims, 6 Drawing Sheets

Specification includes a Sequence Listing.

(56) References Cited

U.S. PATENT DOCUMENTS

| | | | |
|---|---|---|---|
| 7,902,122 | B2 | 3/2011 | Jung et al. |
| 8,071,312 | B2 | 12/2011 | Makarov et al. |
| 8,409,804 | B2 | 4/2013 | Makarov et al. |
| 8,476,018 | B2 | 7/2013 | Brenner |
| 8,481,292 | B2 | 7/2013 | Casbon et al. |
| 8,399,199 | B2 | 12/2013 | Makarov et al. |
| 8,685,678 | B2 | 4/2014 | Casbon et al. |
| 8,715,967 | B2 | 5/2014 | Casbon et al. |
| 8,722,368 | B2 | 5/2014 | Casbon et al. |
| 8,728,737 | B2 | 5/2014 | Makarov et al. |
| 8,728,766 | B2 | 5/2014 | Casbon et al. |
| 8,741,606 | B2 | 6/2014 | Casbon et al. |
| 8,778,610 | B2 | 7/2014 | Makarov et al. |
| 8,835,358 | B2 | 9/2014 | Fodor et al. |
| 9,018,365 | B2 | 4/2015 | Brenner |
| 2004/0209299 | A1* | 10/2004 | Pinter ................ C12N 15/1093 435/6.12 |
| 2007/0020640 | A1 | 1/2007 | McCloskey et al. |
| 2008/0051294 | A1* | 2/2008 | Gormley .............. C12Q 1/6874 506/4 |
| 2009/0068645 | A1 | 3/2009 | Sibson |
| 2010/0120098 | A1* | 5/2010 | Grunenwald .......... C12N 15/10 435/91.2 |
| 2010/0129874 | A1 | 5/2010 | Mitra et al. |
| 2010/0227329 | A1 | 9/2010 | Cuppens |
| 2010/0273219 | A1 | 10/2010 | May et al. |
| 2011/0015096 | A1 | 1/2011 | Chiu |
| 2011/0257031 | A1* | 10/2011 | Bodeau .............. C12N 15/1065 506/9 |
| 2011/0319290 | A1* | 12/2011 | Raymond ............ C12Q 1/6869 506/9 |
| 2012/0015821 | A1 | 1/2012 | Raymond |
| 2012/0028814 | A1 | 2/2012 | Toloue et al. |
| 2012/0142540 | A1* | 6/2012 | Wu ....................... C12Q 1/6874 506/4 |
| 2012/0244525 | A1* | 9/2012 | Hendrickson .......... C07H 21/04 435/6.1 |
| 2013/0184165 | A1* | 7/2013 | Schnable ........... C12N 15/1065 506/2 |
| 2014/0155274 | A1* | 6/2014 | Xie ...................... C12Q 1/6853 506/2 |
| 2014/0227705 | A1 | 8/2014 | Vogelstein et al. |
| 2015/0011396 | A1* | 1/2015 | Schroeder ........... C12Q 1/6855 506/2 |
| 2015/0044687 | A1 | 2/2015 | Schmitt et al. |
| 2016/0208322 | A1* | 7/2016 | Anderson .............. C12N 15/10 |

FOREIGN PATENT DOCUMENTS

| | | | | |
|---|---|---|---|---|
| WO | WO 2011/156529 | | 12/2011 | |
| WO | WO2012103154 | | 8/2012 | |
| WO | WO-2012103154 A1 * | | 8/2012 | .......... C12Q 1/6806 |
| WO | WO 2012/129363 | | 9/2012 | |

OTHER PUBLICATIONS

GeneLink, Adenylation-5' (rApp), available at http://www.genelink.com/newsite/products/mod_detail.asp?modid=151, accessed Sep. 14, 2020.*

Chenchik et al., "Full-length cDNA cloning and determination of mRNA 5' and 3' ends by amplification of adaptor-ligated cDNA," *Biotechniques*, 21(3):526-534, 1996.

Oyola et al., "Optimizing Illumina next-generation sequencing library preparation for extremely AT-biased genomes," *BMC Genomics*, 13:1, 2012.

Pareek et al., "Sequencing technologies and genome sequencing," *J. Appl. Genet.*, 52(4):413-435, 2011.

PCT International Search Report and Written Opinion issued in International Patent Application No. PCT/US2013/068468, dated Feb. 5, 2014.

Siebert et al., "An Improved PCR Method for Walking in Uncloned Genomic DNA," *Nucleic Acids Research*, 23:1087-1088, 1995.

Thudi et al., "Current state-of-art of sequencing technologies for plant genomics research," *Brief Funct. Genomics*, 11(1):3-11, 2012.

* cited by examiner

BARCODING NUCLEIC ACIDS

The present application claims the priority benefit of U.S. provisional application No. 61/722,357, filed Nov. 5, 2012, the entire contents of which are incorporated herein by reference.

The sequence listing that is contained in the file named "RUBCP0031WO_ST25.txt", which is 2 KB (as measured in Microsoft Windows-k) and was created on Nov. 5, 2013, is filed herewith by electronic submission and is incorporated by reference herein.

BACKGROUND OF THE INVENTION

1. Field of the Invention

The present invention relates generally to the fields of molecular biology and nucleic acid sequencing. More particularly, it concerns methods of barcoding nucleic acids.

2. Description of Related Art

Barcodes can be used to identify nucleic acid molecules, for example, where sequencing can reveal a certain barcode coupled to a nucleic acid molecule of interest. In some instances, a sequence-specific event can be used to identify a nucleic acid molecule, where at least a portion of the barcode is recognized in the sequence-specific event, e.g., at least a portion of the barcode can participate in a ligation or extension reaction. The barcode can therefore allow identification, selection or amplification of gDNA molecules that are coupled thereto.

One method to couple a barcode to nucleic acid molecules of interest includes preparation of an Ion gDNA fragment library, as described by Life Technologies for the Ion Torrent System. In this method, fragments of gDNA are ligated to adaptors, where at least one end of each fragment of genomic DNA is ligated to an adaptor including a barcode. The ligated adaptors and gDNA fragments may be nick repaired, size selected, and amplified using PCR with primers directed to the adaptors to produce an amplified library. For example, ligation adaptors including 16 different barcodes can be used to prepare 16 different gDNA samples, each with a unique barcode, such that either each sample can be amplified separately by PCR using the same PCR primers and then pooled (mixed together) or each sample can be pooled first and then simultaneously amplified using the same PCR primers. As a result each gDNA sample can be identified by its attached unique barcode. However, the number of different ligation adaptors needed is equal to the number of barcodes. For example, the production of 256 sample libraries capable of being sequenced as a mixture would require 256 different ligation adapters.

SUMMARY OF THE INVENTION

Embodiments of the present invention provide methods of making dual barcoded nucleic acid molecule for sequencing. Having a first and a second barcode on the same end of a nucleic acid molecule may permit a sequencing read to begin with the second barcode, continue through the first barcode and then into the nucleic acid molecule. Identification of the second barcode, first barcode, and sequence of the nucleic acid molecule may therefore be obtained in a single read as opposed to having to provide a sequencing read from each end of the nucleic acid molecule in order to read the sequence of a single barcode back from a distal end of the nucleic acid molecule, as is the case in traditional methods of using dual sequencing barcodes.

As such, one embodiment of the present invention relates to a method of making a dual barcoded nucleic acid molecule comprising: coupling one strand of a stem-loop oligonucleotide to a nucleic acid molecule to form a first barcode coupled nucleic acid molecule, the stem-loop oligonucleotide including an intramolecular inverted repeat and a loop, the inverted repeat including a first barcode; displacing one strand of the stem-loop oligonucleotide from the first barcode coupled nucleic acid molecule by strand displacement or by nick translation polymerization to form a first barcoded nucleic acid molecule; annealing a primer to the first barcoded nucleic acid molecule, the primer including a first portion complementary to the first barcoded nucleic acid molecule and a second portion including a second barcode; and extending the annealed primer to form a dual barcoded nucleic acid molecule, the dual barcoded nucleic acid molecule including the second barcode, the first barcode, and at least a portion of the nucleic acid molecule. In some aspects, the first portion of the primer anneals to the first barcode or to a portion of the first barcode. In other aspects, the first portion of the primer does not anneal within the first barcode. The extending may be performed by using a polymerase, e.g., via polymerase chain reaction or PCR. The nucleic acid molecule may be genomic DNA, cDNA, amplified DNA, a nucleic acid library, or a fragment thereof.

In one embodiment of the invention, there is a method of preparing a nucleic acid molecule, comprising: providing a double stranded nucleic acid molecule; and attaching one strand of a stem-loop oligonucleotide comprising an inverted repeat and a loop to the double stranded nucleic acid molecule to produce an oligonucleotide-attached nucleic acid molecule. The double stranded nucleic acid molecule may be a double stranded DNA molecule, in some embodiments. In specific embodiments, the attaching is further defined as attaching the oligonucleotide to the double stranded nucleic acid molecule under conditions to produce a non-covalent junction, such as a nick, a gap, or a 5' flap structure, in the oligonucleotide-attached nucleic acid molecule. In particular aspects of the invention, the attaching is further defined as ligating. Ligating may be defined as ligating the 3' end of the stem-loop oligonucleotide adaptor to the 5' end of the target nucleic acid molecule. The method may further comprise displacing one strand of the oligonucleotide from the oligonucleotide-attached nucleic acid molecule by strand displacement or by nick translation polymerization. In a specific embodiment, at least part of the oligonucleotide-attached nucleic acid molecule is amplified, such as by polymerase chain reaction, RNA transcription, or strand displacement, for example. Methods of the invention may further comprise amplifying an oligonucleotide-attached nucleic acid molecule, wherein at least part of the stem-loop adaptor's intramolecular inverted repeat is excluded from the amplified oligonucleotide-attached nucleic acid molecule.

Ligating embodiments may be further defined as comprising: generating ligatable ends on the double stranded nucleic acid molecule; generating a ligatable end on the stem-loop oligonucleotide; and ligating one strand of the ligatable end of the stem-loop oligonucleotide to one strand of an end of the nucleic acid molecule, thereby generating a non-covalent junction, such as a nick, a gap, or a 5' flap structure, in the oligonucleotide-attached nucleic acid molecule. In further aspects, the methods comprise generating blunt ends on the nucleic acid molecule; generating a blunt end on the stem-loop oligonucleotide; and ligating one strand of the blunt end of the stem-loop oligonucleotide to one strand of a blunt end of the nucleic acid molecule, thereby generating a nick in the oligonucleotide-ligated nucleic acid molecule.

In some aspects, the method may comprise coupling one strand of a stem-loop oligonucleotide adaptor to each end of the target nucleic acid molecule. In some aspects, the inverted repeat of the stem-loop adaptors coupled to each end of a target nucleic acid molecule may comprise an identical sequence. In this aspect, coupling of the stem-loop adaptors to each end of the target nucleic acid molecule will produce a nucleic acid molecule comprising terminal inverted repeats thereby allowing the molecule to form a stem loop. In other aspects, the inverted repeat of the stem-loop adaptors coupled to each end of a target nucleic acid molecule may not comprise an identical sequence. In this aspect, coupling of the stem-loop adaptors to each end of the target nucleic acid molecule will produce a nucleic acid molecule lacking terminal inverted repeats and therefore the molecule will not be able to form a stem loop.

In additional embodiments, the oligonucleotide-attached nucleic acid molecule comprises a nick having a 3' hydroxy group, wherein there is polymerization from the 3' hydroxy group of at least part of the oligonucleotide-attached nucleic acid molecule.

Strand displacement or nick translation polymerization may be further defined as polymerization that ceases at a non-replicable base or region in the loop or in a region of the stem adjacent to the loop.

In a specific aspect of the invention, the method further comprises the step of digesting the double stranded DNA molecule with an endonuclease to generate DNA fragments, wherein the oligonucleotide becomes ligated to one strand of the DNA fragment and wherein polymerization of an oligonucleotide-ligated DNA fragment excludes at least part of the stem-loop adaptor's intramolecular inverted repeat by subjecting the oligonucleotide-ligated DNA fragment to strand displacement or nick translation polymerization that halts at a base or sequence in the loop or in a region of the stem adjacent to the loop.

In some embodiments, the stem-loop oligonucleotide is further defined as comprising a cleavable base. In particular, in some cases the cleavable base is present in the loop of the oligonucleotide or in a sequence of the stem adjacent to the loop. The cleavable base or sequence may comprise an abasic site or sequence, hexaethylene glycol, and/or a bulky chemical moiety attached to the sugar-phosphate backbone or the base. In specific embodiments, the abasic site or sequence is introduced by one or more enzymes in the single solution. In a further specific embodiment, the loop of the stem-loop oligonucleotide comprises at least one deoxyuridine.

In specific aspects, a 5' end of the stem-loop oligonucleotide lacks a phosphate.

Barcodes, also referred to as "barcodes," can be generated based on selecting a particular nucleic acid sequence. For example, the Illumina™ sequencing can utilize 6 bases to effectively generate 48 different barcodes. The Ion Torrent sequencer (e.g., the Ion Proton™ Sequencer or the Ion PGM™ sequencer) can utilize 6 bases to generate 16 barcodes. In some embodiments, rules may be applied to the generation of bar codes that allow for separate barcodes to be correctly identified even if two errors occur during sequencing. Barcoding is described, e.g., in U.S. Pat. No. 7,902,122 and U.S. Pat. Publn. 2009/0098555. Barcode incorporation by primer extension, for example via PCR may be performed using methods described in U.S. Pat. No. 5,935,793 or US 2010/0227329. In some embodiments, a barcode may be incorporated into a nucleic acid via using ligation, which can then be followed by amplification; for example, methods described in U.S. Pat. Nos. 5,858,656, 6,261,782, U.S. Pat. Publn. 2011/0319290, or U.S. Pat. Publn. 2012/0028814 may be used with the present invention. In some embodiments, one or more bar code may be used, e.g., as described in U.S. Pat. Publn. 2007/0020640, U.S. Pat. Publn. 2009/0068645, U.S. Pat. Publn. 2010/0273219, U.S. Pat. Publn. 2011/0015096, or U.S. Pat. Publn. 2011/0257031.

Although some embodiments incorporate a second bar code into a genomic library generated, e.g., via the methods described in U.S. Pat. No. 7,803,550, methods of the present invention may be used in combination with a wide variety of techniques for generating a nucleic acid library. For example, a second barcode may be incorporated into a fragment of a nucleic acid library, wherein the nucleic acid library was generated with an approach compatible with Illumina sequencing such as a Nextera™ DNA sample prep kit, and additional approaches for generating Illumina next-generation sequencing library preparation are described, e.g., in Oyola et al. (2012). In other embodiments, a nucleic acid library is generated with a method compatible with a SOLiD™ or Ion Torrent sequencing method (e.g., a SOLiD® Fragment Library Construction Kit, a SOLiD® Mate-Paired Library Construction Kit, SOLiD® ChIP-Seq Kit, a SOLiD® Total RNA-Seq Kit, a SOLiD® SAGE™ Kit, a Ambion® RNA-Seq Library Construction Kit, etc.). Additional methods for next-generation sequencing methods, including various methods for library construction that may be used with embodiments of the present invention are described. e.g., in Pareek (2011) and Thudi (2012).

In an additional embodiment, there is a kit housed in a suitable container that comprises one or more compositions of the invention and/or comprises one or more compositions suitable for at least one method of the invention.

Additional embodiments of the invention include a library of DNA molecules prepared by the methods of the invention.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
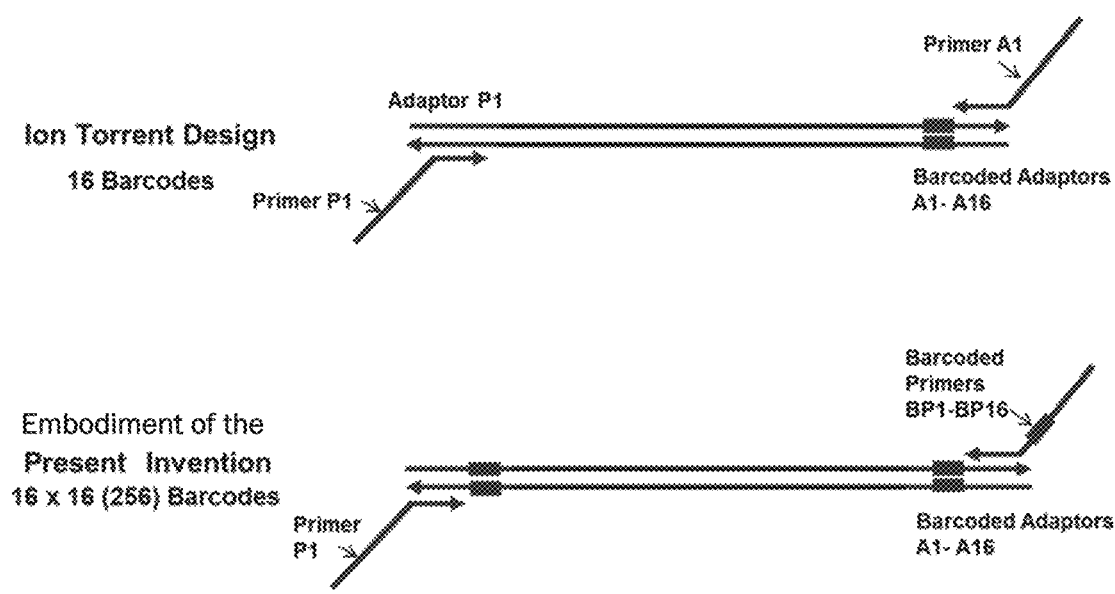
FIG. 1. Schematic comparing use of a single set of barcodes versus the use of first and second sets of barcodes.

The present technology relates to barcoding of nucleic acid molecules. Barcodes, also described as tags, indexing sequences, or identifier codes, include specific sequences that are incorporated into a nucleic acid molecule for identification purposes. For example, synthetic nucleic acid molecules can be joined with genomic DNA (gDNA) by ligation and/or primer extension. The present technology is directed towards nucleic acid molecules having multiple barcodes, in particular, sequential or tandem barcodes. An example of a tandem barcode includes a first barcode coupled to at least one end of a gDNA molecule by a ligation event (e.g., ligation to a synthetic stem-loop adaptor) followed by a second barcode that is coupled to the gDNA by primer extension (e.g., PCR), where the first barcode is proximal to the gDNA molecule (closer to the insert) and the second barcode is distal to the gDNA (further from the insert). Methods of using stem loop adaptor ligation and primer extension or PCR to add additional sequences are described, e.g., in U.S. Pat. No. 7,803,550, which is incorporated by reference herein in its entirety. These methods may be used in embodiments of the present invention to add a first and/or second barcode to a nucleic acid molecule.

Barcodes can be used to identify nucleic acid molecules, for example, where sequencing can reveal a certain barcode coupled to a nucleic acid molecule of interest. In some instances, a sequence-specific event can be used to identify a nucleic acid molecule, where at least a portion of the barcode is recognized in the sequence-specific event, e.g., at least a portion of the barcode can participate in a ligation or extension reaction. The barcode can therefore allow identification, selection or amplification of gDNA molecules that are coupled thereto.

One method to couple a barcode to nucleic acid molecules of interest includes preparation of an Ion gDNA fragment library, as described by Life Technologies for the Ion Torrent System. In this method, fragments of gDNA are ligated to adaptors, where at least one end of each fragment of genomic DNA is ligated to an adaptor including a barcode. The ligated adaptors and gDNA fragments can be nick repaired, size selected, and amplified using PCR with primers directed to the adaptors to produce an amplified library. For example, ligation adaptors including 16 different barcodes can be used to prepare 16 different gDNA samples, each with a unique barcode, such that either each sample can be amplified separately by PCR using the same PCR primers and then pooled (mixed together), or each sample can be pooled first and then simultaneously amplified using the same PCR primers. As a result each gDNA sample can be identified by its attached unique barcode. However, one problem with this approach is that the number of different ligation adaptors needed is equal to the number of barcodes. For example, the production of 256 sample libraries capable of being sequenced as a mixture would require 256 different ligation adapters.

To address this problem, fragments of genomic DNA can be ligated to adaptors having a first set of barcodes, for example, using the stem-loop adaptors and methods as described in U.S. Pat. No. 7,803,550. Adaptors having 16 different barcodes can be generated and may be used, e.g., with an Ion Torrent sequencing system (e.g., the Ion Proton™ Sequencer or the Ion PGM™ sequencer). The ligated adaptors and gDNA fragments having the first set of barcodes can then be subjected to a primer extension reaction or PCR using a primer having a second set of barcodes. The resulting nucleic acid molecules each have one barcode from the first set of barcodes adjacent to one barcode from the second set of barcodes on at least one end of the nucleic acid molecule. The exact number of barcodes may be determined based on the particular application; for example, in some embodiments, the second barcode may utilize six bases to generate, e.g., 16 additional barcodes. Nonetheless, depending on the application and/or sequencing method 1, 2, 3, 4, 5, 6, 7, 8, 9, 10, 11, 12, 13, 14, 15, or 16 or more bases may be utilized to generate the second barcode. In some embodiments, at least 2, at least 3, or 3-16 bases can be used to generate a second barcode.

In some embodiments, the second set of barcodes can include 16 different primers. In this manner, the ligation adaptors having sixteen different barcodes (the first set of barcodes) can be amplified with 16 different primers (directed to the second set of barcodes) to produce 16×16 unique combinations of barcodes, which allows 256 samples to be pooled and multiplexed 256-fold. Use of only 16+16 oligonucleotides to achieve this level of multiplexing is a significant savings of cost and time in producing 256 useful libraries. Preferably, the first barcode and the second barcode may be on the same side of the gDNA (i.e., as part of the same adaptor) and can be sequenced in series with each other and with the gDNA in order to economize on sequencing time and cost.

Additionally, the first barcode may be directly attached to the gDNA, whereas the second barcode may be attached during amplification by PCR. Thus, the first set of barcodes can be used to either: a) tag all members of a gDNA sample with the same barcode or b) tag different members of the gDNA sample with different barcodes. For example, if ligation is performed using a single barcode, then all members of the gDNA will generally carry the same barcode. However, if the ligation adaptor is synthesized with a random or partially-random barcode, different molecules in the gDNA sample will have different barcodes. In the extreme, if the barcode region contains 16 random bases, then 65,536 barcodes may be represented within the ligated nucleic acid library. The barcode may be used to distinguish among different members of the input gDNA library; for example, these methods may be used for independent counting of molecular duplicates in the gDNA library (most of which will have different barcodes) and duplicates created during PCR amplification (most of which will carry identical first barcodes). Partially-random first barcodes can be used to give information about individual samples and about individual molecules.

I. DEFINITIONS

"Amplification," as used herein, refers to any in vitro process for increasing the number of copies of a nucleotide sequence or sequences. Nucleic acid amplification results in the incorporation of nucleotides into DNA or RNA. As used herein, one amplification reaction may consist of many rounds of DNA replication. For example, one PCR reaction may consist of 30-100 "cycles" of denaturation and replication.

"Nucleotide," as used herein, is a term of art that refers to a base-sugar-phosphate combination. Nucleotides are the monomeric units of nucleic acid polymers, i.e., of DNA and RNA. The term includes ribonucleotide triphosphates, such as rATP, rCTP, rGTP, or rUTP, and deoxyribonucleotide triphosphates, such as dATP, dCTP, dUTP, dGTP, or dTTP.

A "nucleoside" is a base-sugar combination, i.e., a nucleotide lacking a phosphate. It is recognized in the art that there is a certain inter-changeability in usage of the terms nucleoside and nucleotide. For example, the nucleotide deoxyuridine triphosphate, dUTP, is a deoxyribonucleoside triphosphate. After incorporation into DNA, it serves as a DNA monomer, formally being deoxyuridylate, i.e., dUMP or deoxyuridine monophosphate. One may say that one incorporates dUTP into DNA even though there is no dUTP moiety in the resultant DNA. Similarly, one may say that one incorporates deoxyuridine into DNA even though that is only a part of the substrate molecule.

"Incorporating," as used herein, means becoming part of a nucleic acid polymer.

"Oligonucleotide," as used herein, refers collectively and interchangeably to two terms of art, "oligonucleotide" and "polynucleotide." Note that although oligonucleotide and polynucleotide are distinct terms of art, there is no exact dividing line between them and they are used interchangeably herein. The term "adaptor" may also be used interchangeably with the terms "oligonucleotide" and "polynucleotide."

"Primer" as used herein refers to a single-stranded oligonucleotide or a single-stranded polynucleotide that is extended by covalent addition of nucleotide monomers during amplification. Often, nucleic acid amplification is based on nucleic acid synthesis by a nucleic acid polymerase. Many such polymerases require the presence of a primer that can be extended to initiate nucleic acid synthesis.

The terms "hairpin" and "stem-loop oligonucleotide" as used herein refer to a structure formed by an oligonucleotide comprised of 5' and 3' terminal regions, which are intramolecular inverted repeats that form a double-stranded stem, and a non-self-complementary central region, which forms a single-stranded loop.

II. ASPECTS OF THE PRESENT INVENTION

Embodiments of the present invention may provide one or more benefits or advantages as follows. Having a first and a second barcode on the same end of a nucleic acid molecule may permit a sequencing read to begin with the second barcode, continue through the first barcode and then into the nucleic acid molecule. Identification of the second barcode, first barcode, and sequence of the nucleic acid molecule may therefore be obtained in a single read as opposed to having to provide a sequencing read from each end of the nucleic acid molecule in order to read the sequence of a single barcode back from a distal end of the nucleic acid molecule, as is the case in traditional methods of using dual sequencing barcodes.

Another advantage in certain embodiments is that the first and second barcodes may be preferably added in two separate steps. This order of addition may significantly increase the possible combinations of encoded sample identity information. In addition, amplification of individual samples with individual PCR primers may reduce the chance of cross-contamination between barcodes due to priming and amplification artifacts as opposed to amplification of pooled samples with a universal PCR primer as currently practiced in some next generation sequencing platforms (FIG. 1). In particular, ligation of the first barcode to at least one end of the nucleic acid molecule may be performed using a short adaptor, e.g., a short stem-loop adaptor. For example, short adaptors have a stem comprising about 14 to about 23 nucleotides whereas long adaptors have a stem of about 24 to about 40 nucleotides.

Qualitative observations and quantitative experiments show that ligation of a single adaptor or two different adaptors designed to contain a common sequence proximal to the ligation site may have a beneficial effect on the ability to preferentially amplify molecules comprising target inserts of controlled size and discriminate against adaptor dimers carrying no insert or molecules comprising short inserts that have little or no information value. This phenomenon is referred to as suppression or suppression PCR. Suppression refers to the selective exclusion of molecules less than a certain size flanked by terminal inverted repeats, due to their inefficient amplification when the primer(s) used for amplification correspond(s) to the entire repeat or a fraction of the repeat (Chenchik et al., 1996; Lukyanov et al., 1999; Siebert et al., 1995; Shagin et al., 1999). The reason for this lies in the equilibrium between productive PCR primer annealing and nonproductive self-annealing of the fragment's complementary ends. At a fixed size of a flanking terminal inverted repeat, the shorter the insert, the stronger the suppression effect and vice versa. Likewise, at a fixed insert size, the longer the terminal inverted repeat, the stronger the suppression effect (Chenchik et al., 1996; Lukyanov et al., 1999; Siebert et al., 1995; Shagin et al., 1999).

By virtue of attaching a terminal inverted repeat to both end of a nucleic acid molecule by ligation and/or primer extension one may achieve precise control over the efficiency of primer annealing and extension of target inserts of desired minimal size versus undesirable adaptor dimers or short insert byproducts as described by U.S. Pat. No. 7,803, 550. Efficiency in attaching the first barcode via adaptor ligation may be utilized for preventing bias and preserving the representation of nucleic acid molecules in a sample. Conversely, coupling the second barcode via primer extension may efficiently employ a long primer including the second barcode.

In this embodiment of the present invention, the target nucleic acid is incubated with an exemplary mixture comprising a stem-loop oligonucleotide with 3' recessed, 3' protruding, or blunt end; a 3' proofreading DNA polymerase (Klenow fragment of the DNA polymerase I, T4 DNA polymerase, etc.); T4 DNA ligase; ATP; and dNTPs. Four exemplary enzymatic reactions are taking place simultaneously: "polishing" of the DNA ends and the oligonucleotide double-stranded stem-region; ligation of the oligonucleotide 3' end to the 5' phosphate of the DNA leaving a nick between the 3' end of DNA and the 5' end of the oligonucleotide double-stranded stem-region; polymerase extension of the 3' DNA end that propagates toward the end of the stem-loop oligonucleotide; and a strand-displacement reaction within the oligonucleotide stem region. This process results in a library of DNA fragments with inverted repeat adaptors at their ends that include the first barcode sequence.

III. METHODS OF THE PRESENT INVENTION

The following outline provides further details relating to the methods and compositions of the present technology. All particular examples provided are understood to be non-limiting examples.

A. Preparation of Nucleic Acid Molecules of Interest

A nucleic acid molecule of interest can be a single nucleic acid molecule or a plurality of nucleic acid molecules. Also, a nucleic acid molecule of interest can be of biological or synthetic origin. Examples of nucleic acid molecules include genomic DNA, cDNA, RNA, amplified DNA, a pre-existing nucleic acid library, etc.

A nucleic acid molecule of interest may be subjected to various treatments, such as repair treatments and fragmenting treatments. Fragmenting treatments include mechanical, sonic, chemical, enzymatic, degradation over time, etc. Repair treatments include nick repair via extension and/or ligation, polishing to create blunt ends, removal of damaged bases such as deaminated, derivatized, abasic, or crosslinked nucleotides, etc. A nucleic acid molecule of interest may also be subjected to chemical modification (e.g., bisulfite conversion, methylation/demethylation), extension, amplification (e.g., PCR, isothermal, etc.), etc.

B. First Barcode Coupling

A first barcode or a first set of barcodes may be coupled to at least one end of the nucleic acid molecule of interest. In some aspects, the first barcode may be provided within a stem-loop adaptor, or a first set of barcodes may be provided as a population of stem-loop adaptors. A stem-loop adaptor may comprise a stem-loop adaptor as described by U.S. Pat. No. 7,803,550. In some aspects, a stem-loop adaptor may include a barcode within the stem portion of the stem-loop adaptor. In some aspects, the loop portion of a stem-loop adaptor may include a cleavable replication stop.

In some aspects, a stem-loop adaptor including the barcode may be coupled to one end of a target nucleic acid molecule or to both ends of a target nucleic acid molecule. In some aspects, the intramolecular inverted repeat of the stem-loop adaptors coupled to each end of a target nucleic acid molecule may comprise an identical sequence. In this aspect, coupling of the stem-loop adaptors to each end of the target nucleic acid molecule will produce a nucleic acid molecule comprising terminal inverted repeats thereby allowing the molecule to form a stem loop. In other aspects, the intramolecular inverted repeat of the stem-loop adaptors coupled to each end of a target nucleic acid molecule may not comprise an identical sequence. In this aspect, coupling of the stem-loop adaptors to each end of the target nucleic acid molecule will produce a nucleic acid molecule lacking terminal inverted repeats and therefore the molecule will not be able to form a stem loop.

In some aspects, a stem-loop adaptor including the barcode may be coupled to the nucleic acid molecule via ligation to the 5' end of the nucleic acid molecule, for example, by blunt-end ligation. Ligating the stem-loop adaptor to one or both ends of a target nucleic acid molecule may result in nick formation. Said one or more nicks may be removed from the ligated stem-loop adaptor and the nucleic acid molecule.

In some aspects, an extension reaction may extend the 3' end of the nucleic acid molecule through the stem-loop adaptor where the loop portion is cleaved at the cleavable replication stop.

C. Second Barcode Coupling

A second barcode or a second set of barcodes may be coupled to the first barcode or the first set of barcodes that is/are coupled to the nucleic acid molecule(s). In this manner, the first barcode may be an intermediate of the nucleic acid molecule and the second barcode. In some aspects, the second barcode may be provided within a primer, or a second set of barcodes may be provided as a population of primers. In some aspects, primer extension or PCR may be used to incorporate the second barcode. In some aspects, the primer may include a 3' portion and a 5' portion, where the 3' portion may anneal to a portion of the first barcode and the 5' portion comprises the second barcode.

Additional information regarding the methods may be found in Ausubel et al. (2003) or Sambrook et al. (1989). As would be recognized by one of skill in the art, various parameters may be manipulated to optimize preparation of a nucleic acid of interest, primer extension, or PCR to incorporate a second barcode.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Dual Inline Barcoding Adaptor Sequences for DNA Sequencing

FIG. 1 provides a schematic comparing the use of a single set of barcodes (e.g., Ion Torrent System) versus the use of first and second sets of barcodes in embodiments of the present technology. The primers are shown to bind to sequences outside the first barcode; however, in some embodiments the primer may bind to the first barcode or even to gDNA sequences. In the aspects of present invention, the ligation may be to a unique adaptor molecule (e.g., a stem loop) that is added to both ends of the gDNA, or two (or more) distinct adaptor molecules that have different sequences. For purposes of reducing background from adaptor dimers, if different adaptor molecules are used they may preferably have a common sequence that will suppress PCR amplification of very short molecules, including adaptor dimers.

Figure 2:
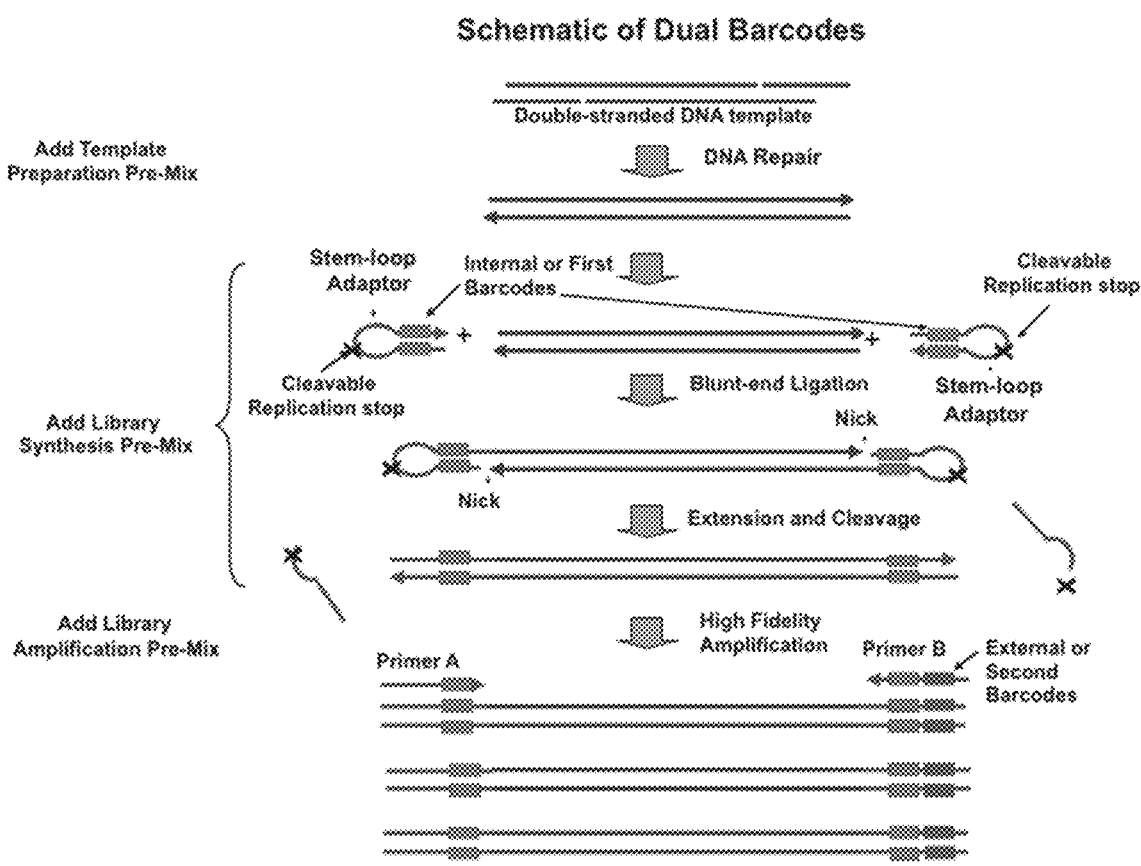
FIG. 2. Illustration of the use of stem-loop adaptors to add the first barcode, further followed by PCR amplification to add the second barcode.

FIG. 2 illustrates a specific embodiment of the invention that utilizes stem-loop adaptors and methods as described in U.S. Pat. No. 7,803,550 to add adaptors with the first bar code. The method is further followed by PCR amplification to add the second barcode.

Figure 3:
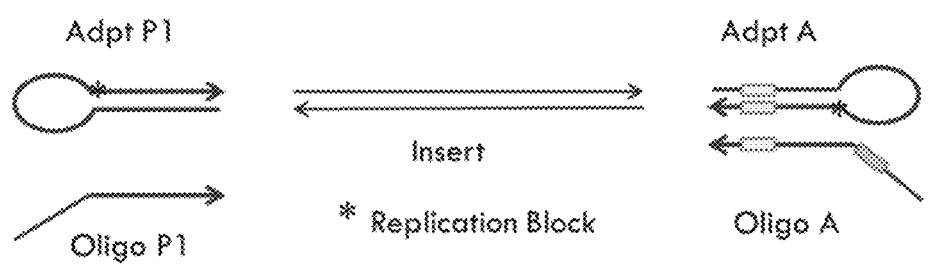
FIG. 3. Illustration of adaptors containing tandem dual barcodes but do not generate terminal inverted repeats.

The inventors sought to test Ion Torrent adaptors that contain tandem dual barcodes but that lack sequences to generate terminal inverted repeats. Stem-loop adaptors and PCR primers were designed as shown in FIG. 3 and Table 1. Of note, the present methods may be adapted for use with other next generation sequencing platforms and is not limited to use with the Ion Torrent platform.

TABLE 1

Oligonucleotide Sequences

| Oligo Name | SEQ ID NO: | Sequence |
| --- | --- | --- |
| Ion Adaptor P1 | 1 | ATCACUGACUGCCCATAUUUUUUTATGGGCAGTCGGTGAT |
| Ion PCR Primer P1 | 2 | CCACTACGCCTCCGCTTTCCTCTCTATGGGCAGTCGGTGAT |
| Ion Adaptor A | 3 | ATCCUGGAAUCCTCTTATCUUUUUUGAT<u>AAGAGGATTCCCG</u>GAT |
| Ion PCR Primer A | 4 | CCATCTCATCCCTGCGTGTCTCCGACTCAG<u>CTAAGGTAAC</u>GAT<u>AAGAGGATTCCCGGAT</u> |

Underlining = first barcode;
Underlining with gray background = second barcode.

Template Preparation.

Ten microliters of each DNA sample (0.1 ng/μL Coavrishearted human gDNA) was added to a PCR tube or well. For non-template controls (NTC), 10 μL of nuclease-free water was substituted for the DNA sample. A pre-mix of 2 μL/sample Template Preparation Buffer ((6.5×ATP-free ligase buffer comprising: 325 mM Tris-HCl pH 7.6 @ 25° C., 65 mM MgCl$_2$, 3.25 mM DTT) supplemented with dNTP mix (2.5 mM each dNTP)) and 1 μL/sample Template Preparation Enzyme (End Repair Mix, Enzymatics Cat # Y914-LC-L) was prepared in a separate tube and mixed by pipette. Then, 3 μL of the pre-mix was added to the 10 μL DNA sample in the PCR tube or well and mixed 4-5 times was a pipette set to 8 μL. The final concentration of the reaction components was as follows: 50 mM Tris-HCl pH 7.6 @(25° C., 10 mM MgCl$_2$, 0.5 mM DTT, 385 μM dNTPs, 1×End Repair Enzymes. The PCR plate was centrifuged and incubated in a thermal cycler using the following conditions: 1 cycle at 22° C. for 25 min; 1 cycle at 55° C. for 20 min; hold at 22° C.

Library Synthesis.

Fresh Library Synthesis pre-mix of 1 μL/sample Library Synthesis Buffer (2×ATP-free ligase buffer comprising: 100 mM Tris-HCl pH 7.6 (@ 25° C., 20 mM MgCl$_2$, 1.0 mM DTT supplemented with 15 mM ATP and 15 μM each stem-loop adaptor oligo) and 1 μL/sample Library Synthesis Enzyme Mix (comprising: 1.2 U Uracil DNA Glycosylase (UDG, Enzymatics # G5010L) and 8 U T4 DNA Ligase (Enzymatics #L603-HC-L) per μL) was prepared in a separate tube and mixed by pipette. Then, 2 μL of the Library Synthesis pre-mix were added to each sample and mixed 4-5 times with a pipette set to 10 μL. The final concentration of the reaction components was as follows: 50 mM Tris-HCl pH 7.6 @ 25° C., 10 mM MgCl$_2$, 0.5 mM DTT, 334 μM dNTPs, 1 mM ATP, 1.2 U Uracil DNA Glycosylase, 8 U T4 DNA Ligase, 1 μM each adaptor oligo. The plate was centrifuged and incubated in a thermal cycler using the following conditions: 1 cycle at 22° C. for 40 min; hold at 4° C.

ThruPLEX-FD Library Amplification.

Library Amplification pre-mix of 4.25 μL/sample nuclease-free water, 3.75 μL/sample EvaGreen:FC (9:1), 50.5 μL/sample Library Amplification Buffer (comprising: 150 mM Tris-SO$_4$, pH 8.5@25° C., 120 mM TMAC, 0.75 mM MgCl$_2$, 0.06% w/v Gelatin, supplemented with 0.375 μM of each PCR oligo), and 1.5 μL/sample Library Amplification Enzyme (KAPA HiFi DNA Polymerase (KK2102) at 1 U/ul) was prepared in a separate tube immediately prior to use. Then, 60 μL of the Library Amplification pre-mix was added to each library and mixed 3-4 times with a pipette set to 60 μL. The final concentration of the reaction components was as follows: 100 mM Tris-SO4, pH 8.5 @ 25° C., 80 mM TMAC, 2.5 mM MgCl$_2$, 0.04% w/v Gelatin, 1×EvaGreen, 1×FCD, 1.5 U KAPA HiFi DNA Polymerase, 0.25 μM each PCR oligo. The plates were centrifuged and then incubated in a real-time thermal cycler as follows: 1 cycle at 72° C. for 3 min; 1 cycle at 85° C. for 2 min; 1 cycle at 98° C. for 2 min; 4 cycles of 98° C. for 20 sec, 67° C. for 20 sec, 72° C. for 40 sec; and 4-21 cycles of 98° C. for 20 sec and 72° C. for 50 sec.

Conclusion.

Figure 4:
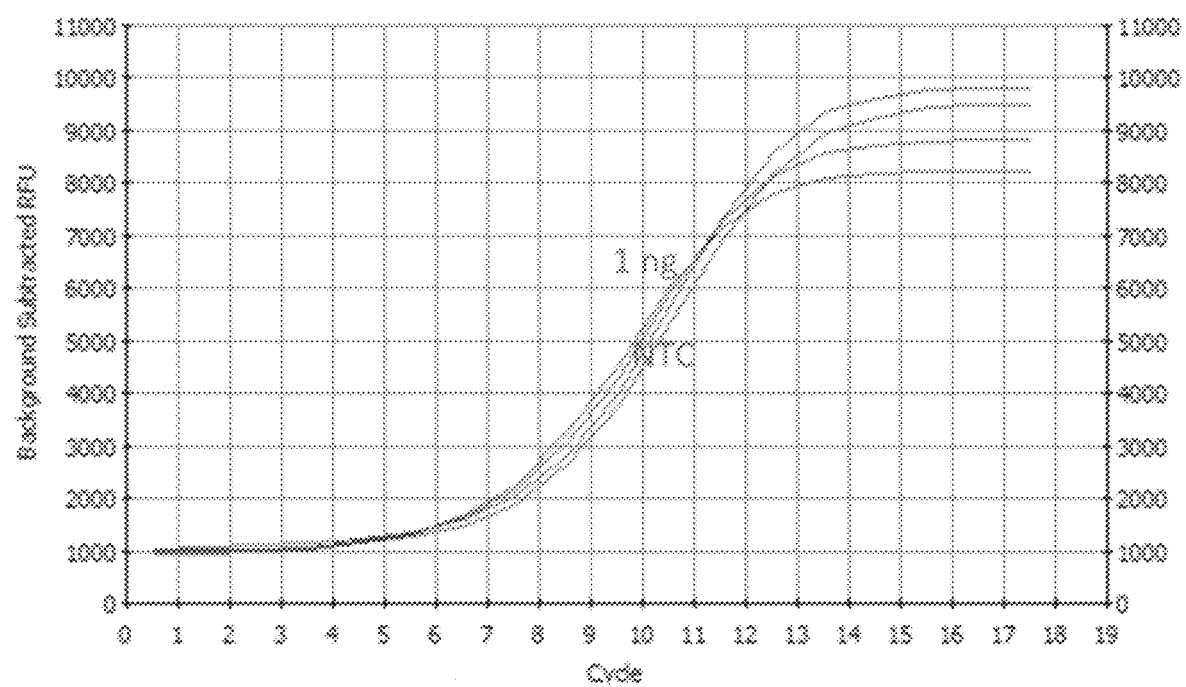
FIG. 4. Results of real-time PCR Library Amplification using tandem dual barcodes without inverted repeats.

Significant amplification of adaptor dimers occurred (FIG. 4). This may be due to the lack of suppression in the construct; therefore, the inventors tested a version containing sequences to generate terminal inverted repeats and comprising the proximal inline barcode.

Figure 5:
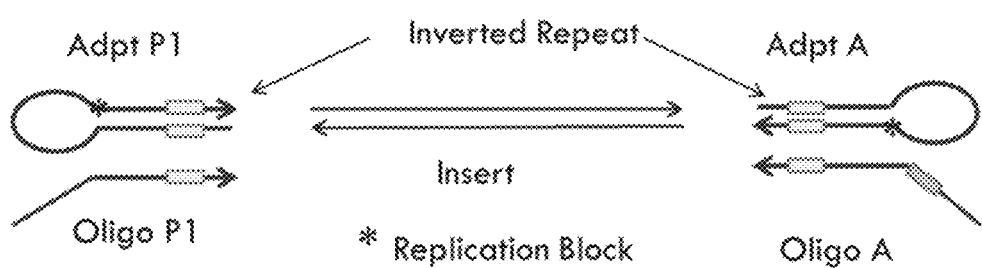
FIG. 5. Illustration of adaptors containing tandem dual barcodes that generate terminal inverted repeats.

Example 2—Dual Inline Barcoding Adaptor Sequences for DNA Sequencing Containing Terminal Inverted Repeats The inventors sought to test Ion adaptors that contain tandem dual barcodes with terminal inverted repeats represented by the second barcode (proximal to the site of ligation). Stem-loop adaptors and PCR primers were designed as shown in FIG. 5 and Table 2.

TABLE 2

Oligonucleotide Sequence for Generating Terminal Inverted Repeats

| Oligo Name | SEQ ID NO: | Sequence |
| --- | --- | --- |
| Ion PCR Oligo P1 | 5 | CCACTACGCCTCCGCTTTCCTCTCTATGGGCAGTCGGTGA TAAGAGGATTCCCGGATTG |
| Ion Universal Adaptor P1/A | 6 | CAATCCUGGAAUCCTCTTATCUUUUUUGAT<u>AAGAGGATTC</u>CCGGATTG |

TABLE 2-continued

Oligonucleotide Sequence for Generating Terminal Inverted Repeats

| Oligo Name | SEQ ID NO: | Sequence |
|---|---|---|
| Ion PCR Primer A | 7 | CCATCTCATCCCTGCGTGTCTCCGACTCAGCTAAGGTAAC GATAAGAGGATTCCCGGATTG |

Underlining = first barcode;
Underlining with gray background = second barcode.

The $T_M$ of the Ion Universal Adaptor P1/A was computed using the Oligo Analyzer (IDT) at 0.25 µM oligo, 100 mM Na⁺, 2.5 mM Mg⁺⁺, and 0.3 mM dNTPs to be 61° C.

Figure 6:
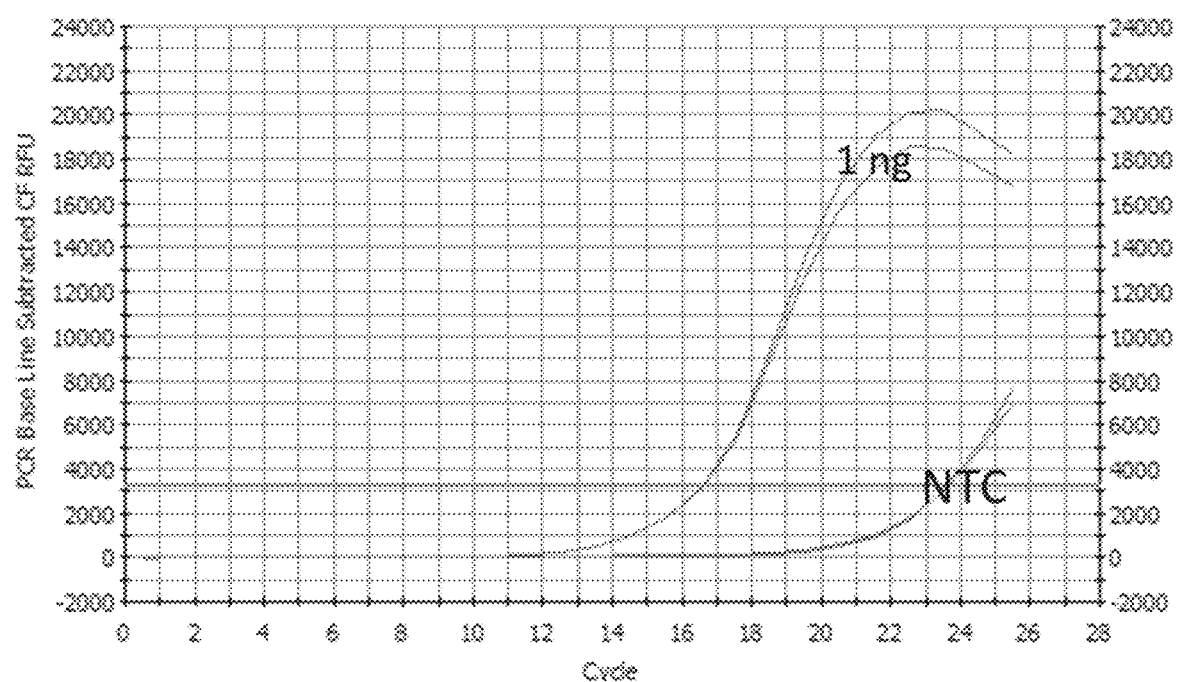
FIG. 6. Results of real-time PCR Library Amplification using tandem dual barcodes with inverted repeats.

The experimental conditions were as described in Example 1, except that the oligonucleotide sequences indicated in Table 2 were used and a single universal stem-loop adaptor (2 µM in the library synthesis reaction) was used to attach terminal inverted repeats to both ends of the DNA fragments. The stem-loop adaptor containing sequences for generating terminal inverted repeats showed significant improvement of signal-to-noise ratio (FIG. 6) over the design containing no such sequences for generating inverted repeats described in Example 1 (FIG. 4).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,858,656
U.S. Pat. No. 5,935,793
U.S. Pat. No. 6,261,782
U.S. Pat. No. 7,803,550
U.S. Pat. No. 7,902,122
U.S. Pat. Publn. No. 2007/0020640
U.S. Pat. Publn. No. 2009/0068645
U.S. Pat. Publn. No. 2010/0227329
U.S. Pat. Publn. No. 2010/0273219
U.S. Pat. Publn. No. 2011/0015096
U.S. Pat. Publn. No. 2011/0257031
U.S. Pat. Publn. No. 2011/0319290
U.S. Pat. Publn. No. 2012/0028814
Ausubel et al., In: *Current Protocols in Molecular Biology*, John Wiley & Sons, N Y, 2003.
Chenchik et al., Full-length cDNA cloning and determination of mRNA 5' and 3' ends by amplification of adaptor-ligated cDNA, *Biotechniques*, 21:526-534, 1996.
Lukyanov et al., Selective suppression of polymerase chain reaction, *Bioorganicheskaya Khimiya*, 25:163-170, 1999.
Oyola et al., Optimizing Illumina next-generation sequencing library preparation for extremely AT-biased genomes, *BMC Genomics*, 13:1, 2012
Pareek et al., Sequencing technologies and genome sequencing, *J. Appl. Genet.*, 52(4):413-435, 2011.
Sambrook et al., In: *Molecular cloning: a laboratory manual*. 2$^{nd}$ Ed., Cold Spring Harbor Laboratory Press, Cold Spring Harbor, N.Y., 1989.
Shagin et al., Regulation of average length of complex PCR product, *Nucleic Acids Research*, 27, e23, 1999.
Siebert et al., An Improved PCR Method for Walking in Uncloned Genomic DNA, *Nucleic Acids Research*, 23:1087-1088, 1995.
Thudi et al., Current state-of-art of sequencing technologies for plant genomics research, *Brief Funct. Genomics.*, 11(1):3-11, 2012.

What is claimed is:

1. An at least partially double-stranded oligonucleotide adaptor, the adaptor comprising:
a stem-loop oligonucleotide comprising an intramolecular inverted repeat, a loop, and a cleavable base or sequence comprising deoxyuridine, an abasic site, or hexaethylene glycol, wherein the inverted repeat includes a barcode, wherein the 5' end of the double-stranded oligonucleotide adaptor consists of a nucleotide that lacks a phosphate.

2. The adaptor according to claim 1, wherein the loop of the stem-loop oligonucleotide comprises the cleavable base or sequence.

3. The adaptor according to claim 2, wherein the cleavable base is deoxyuridine.

4. The adaptor according to claim 1, wherein the barcode comprises a known or partially known sequence.

5. The adaptor according to claim 1, wherein the loop of the stem-loop oligonucleotide adaptor or a region of the stem adjacent to the loop of the stem-loop oligonucleotide adaptor comprises a replication stop.

6. The adaptor according to claim 5, wherein the replication stop is a cleavable replication stop.

* * * * *

SEQUENCE LISTING

<160> NUMBER OF SEQ ID NOS: 7

<210> SEQ ID NO 1
<211> LENGTH: 40
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(40)
<223> OTHER INFORMATION: n is deoxyuridine

<400> SEQUENCE: 1
atcacngacn gcccatannn nnntatgggc agtcggtgat        40

```
<210> SEQ ID NO 2
<211> LENGTH: 41
<212> TYPE: DNA
<213> ORGANISM: Artificial Sequence
<220> FEATURE:
<223> OTHER INFORMATION: Synthetic primer

<400> SEQUENCE: 2
ccactacgcc tccgctttcc tctctatggg cagtcggtga t                 41

<210> SEQ ID NO 3
<211> LENGTH: 44
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(44)
<223> OTHER INFORMATION: n is deoxyuridine

<400> SEQUENCE: 3
atccnggaan cctcttatcn nnnnngataa gaggattccc ggat              44

<210> SEQ ID NO 4
<211> LENGTH: 59
<212> TYPE: DNA
<213> ORGANISM: Artificial Sequence
<220> FEATURE:
<223> OTHER INFORMATION: Synthetic primer

<400> SEQUENCE: 4
ccatctcatc cctgcgtgtc tccgactcag ctaaggtaac gataagagga ttcccggat     59

<210> SEQ ID NO 5
<211> LENGTH: 59
<212> TYPE: DNA
<213> ORGANISM: Artificial Sequence
<220> FEATURE:
<223> OTHER INFORMATION: Synthetic primer

<400> SEQUENCE: 5
ccactacgcc tccgctttcc tctctatggg cagtcggtga taagaggatt cccggattg    59

<210> SEQ ID NO 6
<211> LENGTH: 48
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(48)
<223> OTHER INFORMATION: n is deoxyuridine

<400> SEQUENCE: 6
caatccngga ancctcttat cnnnnnngat aagaggattc ccggattg          48

<210> SEQ ID NO 7
<211> LENGTH: 61
<212> TYPE: DNA
<213> ORGANISM: Artificial Sequence
<220> FEATURE:
<223> OTHER INFORMATION: Synthetic primer
```

```
<400> SEQUENCE: 7
ccatctcatc cctgcgtgtc tccgactcag ctaaggtaac gataagagga ttcccggatt    60
g                                                                    61
```